(12) United States Patent
Gelfand et al.

(10) Patent No.: US 6,978,174 B2
(45) Date of Patent: Dec. 20, 2005

(54) METHODS AND DEVICES FOR RENAL NERVE BLOCKING

(75) Inventors: Mark Gelfand, New York, NY (US); Howard R. Levin, Teaneck, NJ (US)

(73) Assignee: Ardian, Inc., Menlo Park, CA (US)

( * ) Notice: Subject to any disclaimer, the term of this patent is extended or adjusted under 35 U.S.C. 154(b) by 0 days.

(21) Appl. No.: 10/900,199

(22) Filed: Jul. 28, 2004

(65) Prior Publication Data

US 2005/0192638 A1    Sep. 1, 2005

Related U.S. Application Data

(63) Continuation-in-part of application No. 10/408,665, filed on Apr. 8, 2003.

(60) Provisional application No. 60/370,190, filed on Apr. 8, 2002, provisional application No. 60/415,575, filed on Oct. 3, 2002, provisional application No. 60/442,970, filed on Jan. 29, 2003.

(51) Int. Cl.[7] ................................................. A61N 1/08
(52) U.S. Cl. ..................... 607/3; 604/890.1; 604/891.1
(58) Field of Search ......................... 607/3; 604/890.1, 604/891.1, 131, 151, 522

(56) References Cited

U.S. PATENT DOCUMENTS

| | | | |
|---|---|---|---|
| 3,987,790 A | 10/1976 | Eckenhoff et al. | |
| 4,011,861 A | 3/1977 | Enger | |
| 4,360,019 A | 11/1982 | Portner et al. | |
| 4,405,305 A | 9/1983 | Stephen et al. | |
| 4,487,603 A | 12/1984 | Harris | |
| 4,530,840 A | 7/1985 | Tice et al. | |
| 4,608,985 A | 9/1986 | Crish et al. | |
| 4,649,936 A | 3/1987 | Ungar et al. | |
| 4,692,147 A | 9/1987 | Duggan | |
| 4,715,852 A | 12/1987 | Reinicke et al. | |
| 4,816,016 A | 3/1989 | Schulte et al. | |
| 4,852,573 A | 8/1989 | Kennedy | |
| 4,865,845 A | 9/1989 | Eckenhoff et al. | |
| 4,981,146 A | 1/1991 | Bertolucci | |
| 5,057,318 A | 10/1991 | Magruder et al. | |
| 5,059,423 A | 10/1991 | Magruder et al. | |
| 5,061,492 A | 10/1991 | Okada et al. | |
| 5,112,614 A | 5/1992 | Magruder et al. | |
| 5,137,727 A | 8/1992 | Eckenhoff | |
| 5,188,837 A | 2/1993 | Domb | |
| 5,199,428 A | 4/1993 | Obel et al. | |
| 5,215,086 A | 6/1993 | Terry, Jr. et al. | |
| 5,231,988 A | 8/1993 | Wernicke et al. | |
| 5,234,692 A | 8/1993 | Magruder et al. | |
| 5,234,693 A | 8/1993 | Magruder et al. | |
| 5,251,634 A | 10/1993 | Weinberg | |
| 5,251,643 A | 10/1993 | Osypka | |
| 5,263,480 A | 11/1993 | Wernicke et al. | |
| 5,269,303 A | 12/1993 | Wernicke et al. | |

(Continued)

OTHER PUBLICATIONS

"Effects of Long Term Renal Sympathetic Denervation On Heart Failure After Myocardial Infarction In Rats", Takashy Nozawa et al, Heart Vessels (2002), 16:51-56.

(Continued)

Primary Examiner—Mark Bockelman
(74) Attorney, Agent, or Firm—Perkins Coie LLP (57) ABSTRACT

A method and apparatus for treatment of cardiac and renal diseases associated with the elevated sympathetic renal nerve activity by implanting a device to block the renal nerve signals to and from the kidney. The device can be a drug pump eluting implant for targeted delivery of a nerve-blocking agent to the periarterial space of the renal artery.

25 Claims, 9 Drawing Sheets

U.S. PATENT DOCUMENTS

| | | |
|---|---|---|
| 5,282,468 A | 2/1994 | Klepinski |
| 5,299,569 A | 4/1994 | Wernicke et al. |
| 5,335,657 A | 8/1994 | Terry, Jr. et al. |
| 5,358,514 A | 10/1994 | Schulman et al. |
| 5,400,784 A | 3/1995 | Durand et al. |
| 5,429,634 A | 7/1995 | Narciso, Jr. |
| 5,458,631 A | 10/1995 | Xavier |
| 5,540,730 A | 7/1996 | Terry, Jr. et al. |
| 5,571,150 A | 11/1996 | Wernicke et al. |
| 5,589,192 A | 12/1996 | Okabe et al. |
| 5,618,563 A | 4/1997 | Berde et al. |
| 5,626,862 A | 5/1997 | Brem et al. |
| 5,634,462 A | 6/1997 | Tyler et al. |
| 5,689,877 A | 11/1997 | Grill, Jr. et al. |
| 5,700,282 A | 12/1997 | Zabara |
| 5,700,485 A | 12/1997 | Berde et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,800,464 A | 9/1998 | Kieval |
| 5,814,079 A | 9/1998 | Kieval |
| 5,824,027 A | 10/1998 | Hoffer et al. |
| 5,836,935 A | 11/1998 | Ashton et al. |
| 5,843,069 A | 12/1998 | Butler et al. |
| 5,891,181 A | 4/1999 | Zhu |
| 5,906,817 A * | 5/1999 | Moullier et al. ......... 424/93.21 |
| 5,913,876 A | 6/1999 | Taylor et al. |
| 5,916,239 A | 6/1999 | Geddes et al. |
| 6,006,134 A | 12/1999 | Hill et al. |
| 6,058,331 A | 5/2000 | King |
| 6,073,048 A | 6/2000 | Kieval et al. |
| 6,077,227 A | 6/2000 | Miesel et al. |
| 6,122,548 A | 9/2000 | Starkebaum et al. |
| 6,178,349 B1 | 1/2001 | Kieval |
| 6,192,889 B1 | 2/2001 | Morrish |
| 6,238,702 B1 | 5/2001 | Berde et al. |
| 6,269,269 B1 | 7/2001 | Ottenhoff et al. |
| 6,272,383 B1 | 8/2001 | Grey et al. |
| 6,292,695 B1 | 9/2001 | Webster, Jr. et al. |
| 6,304,777 B1 | 10/2001 | Ben-Haim et al. |
| 6,306,423 B1 | 10/2001 | Donovan et al. |
| 6,326,020 B1 | 12/2001 | Kohane et al. |
| 6,366,815 B1 | 4/2002 | Haugland et al. |
| 6,393,324 B2 | 5/2002 | Gruzdowich et al. |
| 6,405,079 B1 | 6/2002 | Ansarinia |
| 6,415,183 B1 | 7/2002 | Scheiner et al. |
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,473,644 B1 | 10/2002 | Terry, Jr. et al. |
| 6,522,926 B1 | 2/2003 | Kieval et al. |
| 6,524,607 B1 | 2/2003 | Goldenheim et al. |
| 6,534,081 B2 | 3/2003 | Goldenheim et al. |
| 6,692,738 B2 | 2/2004 | MacLaughlin et al. |
| 6,845,267 B2 * | 1/2005 | Harrison et al. ............... 607/3 |
| 2002/0032468 A1 | 3/2002 | Hill et al. |
| 2002/0038137 A1 | 3/2002 | Stein |
| 2002/0072782 A1 | 6/2002 | Osorio et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0165586 A1 | 11/2002 | Hill et al. |
| 2002/0188325 A1 | 12/2002 | Hill et al. |
| 2003/0004549 A1 | 1/2003 | Hill et al. |
| 2003/0040774 A1 | 2/2003 | Terry, Jr. et al. |
| 2003/0045909 A1 | 3/2003 | Gross et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |

OTHER PUBLICATIONS

"Interaction Between Renal Sympathetic Nerves and The Renin-Angiotensin System In The Control of Renal Function", GF DiBona, Hypertension, 2000; 36:1083-1088.

"Renal Denervation Prevents and Reverses Hyperinsulinemia-Induced Hypertension In Rats", Wann-Chu Huang et al, Hypertension 1998, 32:249-254.

"Renal Afferent Denervation Prevents the Progression of Renal Disease in the Renal Ablation Model of Chronic Renal Failure In The Rat", VM Campese et al., American Journal of Kidney Diseases vol. 26, No. 5, 1995, pp. 861-865.

"Functionally Specific Renal Sympathetic Nerve Fibers: Role In Cardiovascular Regulation", GF DiBona, American Journal of Hypertension, 2001, 14:163S-170S.

U.S. Appl. No. 10/408,665, Levin et al.
U.S. Appl. No. 60/408,665, Cutler et al.
U.S. Appl. No. 60/370,190, Levin et al.
U.S. Appl. No. 60/415,575, Levin et al.
U.S. Appl. No. 60/442,970, Levin et al.
U.S. Appl. No. PCT/US04/38498, G&L Consulting, Inc., dated Feb. 18, 2005.

Heart Disease, 5th ed., E. Braunwald, Chpts. 16 (pp. 480-481); 16 (pp. 824-825); 37 (pp. 1184-1284); 62 (pp. 1923-1925); (1997).

Charles Berde "Mechanisms of Local Anesthetics" (Anesthesia, 5th addition, R.D. Miller, editor, Churchill-Livingston, Philadelphia 2000, pp. 491-521).

Syncromed Pump made by Medtronic, Inc. (Shoreview, MN).

Gerald DiBona "Neural Control of the Kidney: Functionally Specific Renal Sympathetic Nerve Fibers," Am J Physiol Regulatory Integrative Comp Physiol, 2000, 279: R1517-R1524, The American Physiological Society, Behtesda, MD.

Hopp, Francis A. et al., "Respiratory Responses to Selective Blockade of Carotid Sinus Baroreceptors in the Dog," Am J Physiol Regul Integr Comp Physiol, 1998, 275:10-18, American Physiological Society, Bethesda, MD.

* cited by examiner

METHODS AND DEVICES FOR RENAL NERVE BLOCKING

This application is a continuation-in-part of U.S. patent application Ser. No. 10/408,665 filed Apr. 8, 2003, which claims the benefit of U.S. Provisional Application No. 60/370,190, filed Apr. 8, 2002, U.S. Provisional Application No. 60/415,575, filed Oct. 3, 2002, and U.S. Provisional Application No. 60/442,970, filed on Jan. 29, 2003, which are incorporated herein by reference.

FIELD OF THE INVENTION

This invention relates to devices and methods for local drug delivery, and in particular is directed to an implantable system for targeted delivery of a nerve blocking agent to the periarterial space of the renal artery for the purpose of blocking the renal nerve plexus, methods for implanting same, and methods and devices for treating diseases. The invention directs the nerve-blocking agent towards the nerve, prevents dissipation of the agent in the surrounding tissue and provides fixation of the drug delivery mechanism in the surrounding tissue.

BACKGROUND OF THE INVENTION

Hypertension (HTN) and congestive heart failure (CHF) are the most important problems in contemporary cardiology. These chronic diseases account for most cardiovascular morbidity and mortality, and, despite much progress, remain therapeutic challenges. The cornerstone of therapy for both HTN and CHF includes the use primarily oral and intravenous drugs acting directly or indirectly on the kidney, such as angiotensin converting enzyme (ACE) inhibitors and diuretics, with the amount of each drug used dependent on the stage of the disease. While drug therapy is effective in the earliest stages of HTN and CHF, there is no truly effective drug treatment for the mid-to-later stages of these diseases.

HTN and CHF have many different initial causes. Irrespective of initial cause, both diseases follow a common pathway in their progression to end-stage disease, primarily as the result of excessive activity of the renal nerve. It has been shown in accepted animal models that renal denervation can control HTN and improve symptoms and slow down the progression of CHF. However, no drug or device therapies currently exist that can provide long-term, clinically usable blocking of renal nerve activity in humans. The only available clinical method of renal denervation is an invasive surgical procedure, technically difficult and of limited use, as the nerve quickly regenerates.

Of particular significance for this invention is the CHF condition that develops in many patients following a myocardial infarction (MI). Coronary artery disease causes approximately 70% of congestive heart failure. Acute MI due to obstruction of a coronary artery is a common initiating event that can lead ultimately to heart failure. This process by which this occurs is referred to as remodeling and is described in the text Heart Disease, 5th ed., E. Braunwald, Ch. 37 (1997). Remodeling after a myocardial infarction involves two distinct types of physical changes to the size, shape and thickness of the left ventricle. The first, known as infarct expansion, involves a localized thinning and stretching of the myocardium in the infarct zone. This myocardium can go through progressive phases of functional impairment, depending on the severity of the infarction. These phases reflect the underlying myocardial wall motion abnormality and include an initial dyssynchrony, followed by hypokinesis, akinesis, and finally, in cases that result in left ventricular aneurysm, dyskinesis. This dyskinesis has been described as "paradoxical" motion because the infarct zone bulges outward during systole while the rest of the left ventricle contracts inward. Consequently, end-systolic volume in dyskinetic hearts increases relative to nondyskinetic hearts.

The second physical characteristic of a remodeling left ventricle is the attempted compensation of noninfarcted region of myocardium for the infarcted region by becoming hyperkinetic and expanding acutely, causing the left ventricle to assume a more spherical shape. This helps to preserve stroke volume after an infarction. These changes increase wall stress in the myocardium of the left ventricle. It is thought that wall tension is one of the most important parameters that stimulate left ventricular remodeling. In response to increased wall tension or stress, further ventricular dilatation ensues. Thus, a vicious cycle can result, in which dilatation leads to further dilatation and greater functional impairment. On a cellular level, unfavorable adaptations occur as well. This further compounds the functional deterioration.

Takashi Nozawa et al reported the effects of renal denervation in "Effects of long-term renal sympathetic denervation on heart failure after myocardial infarction in rats" published in Heart Vessels (2002) 16: 51–56 Springer-Verlag. In rats the bilateral renal nerves were surgically denervated (cut) (RD) two days before MI was induced by coronary artery legation. Four weeks later, left ventricular (LV) function and sodium excretion were determined. In MI rats, RD improved the reduced sodium excretion. MI RD rats revealed lower LV end-diastolic pressure and greater maximum dP/dt as compared with those of MI innervation (INN) rats. LV end-diastolic and end-systolic dimensions were significantly smaller and LV fractional shortening was greater in MI RD rats than in MI INN rats.

Inventors described novel methods and devices for reversible minimally invasive modulation of the renal nerve in copending applications. This application describes novel drug delivery methods and integrated physiological drug delivery and sensing systems that provide a significantly more effective method of blocking the renal nerve for the purpose of treating HTN and CHF than are currently available. The objective of this invention is a fully implantable device that blocks renal nerve activity of at least one kidney that 1) can be placed in a minimally invasive manner and 2) requires minimal intervention by the patient and physician; and will greatly increase patient compliance leading to a higher overall effectiveness of these therapies. In addition, to HTN and CHF, this method may be applicable to other major diseases such as slowing the progression of chronic renal failure and reducing the number of patients requiring chronic hemodialysis.

Nerve blocking in humans is known and practiced mostly in the field of local anesthesia and pain control. While compounds utilized as general anesthetics reduce pain by producing a loss of consciousness, local anesthetics act via a loss of sensation in the localized area of administration in the body. The mechanism by which local anesthetics induce their effect, while not having been determined definitively, is generally thought to be based upon the ability to locally interfere with the initiation and transmission of a nerve impulse, e.g., interfering with the initiation and/or propagation of a depolarization wave in a localized area of nerve tissue. The actions of local anesthetics are general, and any tissue where nerve conduction, e.g., cell membrane depolarization occurs can be affected by these drugs. Thus, nervous tissue mediating both sensory and motor functions can be similarly affected by local anesthetics. Neurotoxins are the chemicals that when applied to nerve tissue in extremely small amounts can block a nerve for a period of time that significantly exceeds that achieved with local anesthetics. They are also more toxic and potentially more dangerous to the patient than local anesthetics.

Different devices and formulations are known in the art for administration of local anesthetics. For example, local anesthetics can be delivered in solution or suspension by means of injection, infusion, infiltration, irrigation, topically and the like. Injection or infusion can be carried out acutely, or if prolonged local effects are desired, localized anesthetic agents can be administered continuously by means of a gravity drip or infusion pump. Thus, local anesthetics such as bupivacaine have been administered by continuous infusion, e.g., for prolonged epidural or intrathecal (spinal) administration. For prolonged control of pain fully implantable pumps have been proposed and implemented. These pumps can store a certain amount of drug and a physician periodically refills those. Several authors proposed drug eluting implants for control of pain and muscle spasms that slowly release an anesthetic agent at the site of implantation.

The duration of action of a local anesthetic is proportional to the time during which it is in actual contact with the nervous tissues. Consequently, procedures or formulations that maintain localization of the drug at the nerve greatly prolong anesthesia. Local anesthetics are potentially toxic, both locally and via systemic absorption, yet must be present long enough to allow sufficient time for the localized pain to subside. Therefore, it is of great importance that factors such as the choice of drug, concentration of drug, and rate and site of administration of drug be taken into consideration when contemplating their use for the application to block renal nerve. Charles Berde in "Mechanisms of Local Anesthetics" (Anesthesia, 5th addition, R. D. Miller, editor, Churchill-Livingstone, Philadelphia 2000, pp. 491–521) stipulated that only 1–2% of the total amount of local anesthetic, when delivered by traditional methods, ever reaches the nerve. The rest of the drug is dissipated by circulation of blood that takes the drug away, not towards the nerve. It is therefore the purpose of this invention to maximize the amount of drug directed towards the nerve so as to achieve the effective blockade of the renal nerve with the minimal amount of drug.

Theoretically, a suitable commercially available implantable drug pump such as a Syncromed pump made by Medtronic Inc. (Shoreview, Minn.) can be used to block the renal nerve in a human. The pump can deliver common commercially available solution of a local anesthetic agent such as bupivacaine to the tissue surrounding the renal nerve via an attached catheter. Although feasible, such embodiment of the renal nerve block will have practical limitations. To block a peripheral nerve (for example, for the purpose of a commonly performed brachial plexus block) using conventional techniques the physician typically infiltrates 10–50 ml of bupivacaine or similar anesthetic into the tissue surrounding the targeted nerve. This usually achieves adequate blocking of both sensory and motor signals for 2 to 6 hours. Commercially available bupivacaine marketed as Marcaine or Sensorcaine is available in concentrations of 0.25 to 0.1%. For peripheral (single nerve) blocks concentrations of 0.5 to 0.75% are typically used. There are several reasons why local anesthetics are so diluted. An amino-amide compound such as bupivacaine can be toxic both locally (it is an irritant) and systemically (it depresses the heart). It is generally perceived that a local anesthetic will not be effective below certain minimum concentration and will be toxic above certain maximum concentration.

Implantable drug pumps are commonly equipped with an internal drug storage reservoir of 30 to 50 ml. Bigger reservoirs are possible but impose severe limitations on the physical and clinical acceptability of the implant. If the continuous (24 hour a day 7 days a week) block of the patient's renal nerve is desired, and a conventional peripheral nerve blocking technique is used, the implanted pump reservoir will need to be refilled every day or even more frequently. This is possible but not practical, since refilling of the pump is associated with the skin puncture, causing pain and leading to the risk of local and systemic infection. Also, daily infusion of a large amount of drug can result in a serious risk to the patient's health, especially if the patient has a weak heart. Notably the same drug bupivacaine is effective in a much lower doze when delivered directly to the targeted nerve tissue in the patient's spine. For example, an effective intrathecal (spinal) pain block can be achieved with 2–5 ml of bupivacaine. This observation shows that more targeted delivery of the same drug to the nerve tissue can result in 10 times or more reduction of the amount of drug needed for nerve blocking.

It is therefore the purpose of this invention to provide novel methods and implantable devices that will effectively block renal nerve by targeting the delivery of the selected drug to the nerve, reducing dissipation of the drug into the surrounding tissue, reducing the amount of drug stored in the device and increasing the time interval between the refilling or replacement of the device. It is also the purpose of this invention to enable testing of the effectiveness of the renal nerve blockade and to perform the renal block automatically, intermittently and/or periodically in the clinical scenarios where the continuous block is not desired.

SUMMARY OF THE INVENTION

Surgical denervation of the kidney in experimental animals suggested multiple immediate and long-term benefits for patients with cardiac and renal diseases. The most significant potential beneficial effects are: slowing of the progression of CHF, resolution of fluid overload in CHF by induction or enhancement of diuresis, reduction of remodeling after a myocardial infarct, reduction of hypertension and slowing of the progression of chronic renal disease to dialysis. The benefits are achieved via the reduction of the systemic sympathetic tone causing vasoconstriction of blood vessels, reduction of the load on the heart and the direct effects of denervation on the kidney. Both single kidney denervation and bilateral denervation have potential benefits. Surgical denervation has been previously performed in animals and in few humans to control pain. It requires a major surgery and is ineffective in long term, since renal nerves eventually grow back. Additionally, after the surgical denervation, the renal nerve can re-grow in a pathological way and can cause pain and other serious side effects. Since fibrotic changes at the site of denervation make repeat surgical denervation impossible, patients face the possibility of the removal of the kidney to control the pain.

The inventors suggest an alternative method of reducing or blocking the renal nerve activity in patients by minimally invasive renal nerve modulation. Renal nerve modulation is achieved by controlled infusion of a nerve-blocking agent into the periarterial space of the renal artery of the kidney. The periarterial space is the area surrounding the renal arteries and veins, extending from the aorta and vena cava to and including the area around the kidney itself. Since renal nerves follow the external surface of the renal artery, when an effective concentration of the nerve-blocking agent is present in this periarterial space, the renal nerve activity is substantially reduced or stopped. Methods and devices for both continuous and intermittent periodic blocking of the renal nerve are proposed. These methods and devices provide effective, reversible nerve blocking for a clinically relevant duration of time, while avoiding major surgery and irreparable damage to the nerve that characterize the previously used surgical denervation.

The preferred embodiment devices can be implantable drug pumps or drug eluting implants. Both classes of local drug delivery devices are known. Implanted pumps have been successfully used previously for control of pain by infusion of local anesthetics into the patient's spine. Implantable pumps range from simple reservoirs (ports) implanted under the skin with an attached catheter to sophisticated microprocessor driven programmable devices similar to pacemakers. Drug eluting implants have been used to deliver birth control agents and to prevent restenosis of coronary arteries.

Implanted pumps can also be refilled with drug without surgery using a transdermal port accessible with a needle, though it is preferable to extend the time between refillings to minimize pain and the risk of infection. The programmable implantable pump embodiment also has an advantage of the periodic drug delivery that can be adjusted up or down using a remote communication link. This is particularly significant in treatment of chronic diseases such as CHF where the continuous constant nerve blocking can result in adaptation (resting of the physiologic gain or compensation) and the loss of therapeutic effect.

Drug eluding implants work primarily by diffusion. Drug eluting implants are advantageous in the treatment of a temporary condition such as infarct expansion following acute MI where an implant that blocks the nerve for approximately 30 days and then dissolves on its own can be the best embodiment of the invention.

SUMMARY OF THE DRAWINGS

A preferred embodiment and best mode of the invention is illustrated in the attached drawings that are described as follows.

DETAILED DESCRIPTION OF THE INVENTION

For the proposed clinical use, the capability of the invention is to block the sympathetic activity of the renal nerve of the kidney by controlled local delivery of a nerve-blocking agent with the goal of improving the patient's renal and cardiac function. Elements of the invention are useful for blocking nerves for the purpose other than treating cardiorenal disease and can be applied in other anatomic locations.

A nerve blocking agent is a drug that reduces or blocks conduction of signals by renal nerves. The nerve blocking agents used can be selected from different groups including (1) local anesthetics, (2) ketamine (a well known sedative with nerve blocking properties), (3) tricyclic antidepressants such as amitriptyline, (4) neurotoxins such as tetrodotoxin and saxitoxin or (5) any other class or type of agent that transiently or permanently, partially or completely alters nerve conduction. The terms nerve blocking agent and nerve blocking drug are interchangeable.

Cardiorenal disease is defined as a condition, chronic or acute, that involves both the heart and the kidney. Examples of cardiorenal diseases are hypertension and CHF. Cardiorenal diseases are characterized by the elevated activity of the renal nerve.

For the purpose of this invention, the renal nerve is defined as any individual nerve or plexus of nerves and ganglia that conducts a nerve signal to and/or from the kidney and is anatomically located on the surface of the renal artery, parts of aorta where the renal artery branches from the aorta and/or on branches of the renal artery. The renal nerve generally enters the kidney in the area of the hilum of the kidney, but may enter in any location where a renal artery or branch of the renal artery enters the kidney.

Periarterial space is defined as the space immediately surrounding the renal arteries, renal veins and their branches between the aorta and the hilum of the kidney. The renal fat pad is defined as the adipose tissue or fat that fills the periarterial space and surrounds the renal artery, renal vein, renal nerves and the kidney itself. The renal fascia is the layer of connective tissue that surrounds, envelopes and contains the renal artery, renal vein, renal fatpad and the kidney itself.

An implantable or implanted device (commonly termed an "implant") is an artificial device fully enclosed in the patient's body. It is significant that implants allow the natural skin of the patient to serve as a barrier against infection. An implant can be, for example, a complex electromechanical pump, catheter and port or a drug-releasing polymer. Implantation can be achieved by open surgery, minimally invasive surgery or a transcatheter intervention, whether extravascular, intravascular or combination of any of the above. During the implantation procedure, a surgical instrument or catheter is used to cross the skin, penetrating into the patient's body. The implant is positioned at the desired site and the pathway used to access the site is closed. The site heals and the device is now fully implanted.

An implantable pump is an implantable device that is inserted under the patient's skin and can be refilled using a transdermal needle access. An implantable pump may have an integral catheter or can be equipped with a separate catheter that delivers medication to the periarterial space. Depending on the desired treatment modality, a preferred implantable pump can be programmable, patient controlled or a constant rate device.

A drug eluting implant is a device that is fully implanted in the body that slowly elutes the nerve-blocking agent into the target space. One example of such a space is the renal periarterial space. Another example is inside the renal capsule, or the virtual space between the kidney tissue and the fibrous sheath surrounding the kidney tissues itself. Drug eluting implants work by diffusion and can be biodegradable or not. An osmotic pump is also a drug eluting implant. Different matrixes that serve to slow down the diffusion of the drug into a target space are all called drug eluting implants for the purpose of this invention. These include gels, patches, injectable microspheres, suspensions, solutions or any other matrix that may hold sufficient drug to cause the intended effect.

Figure 1:
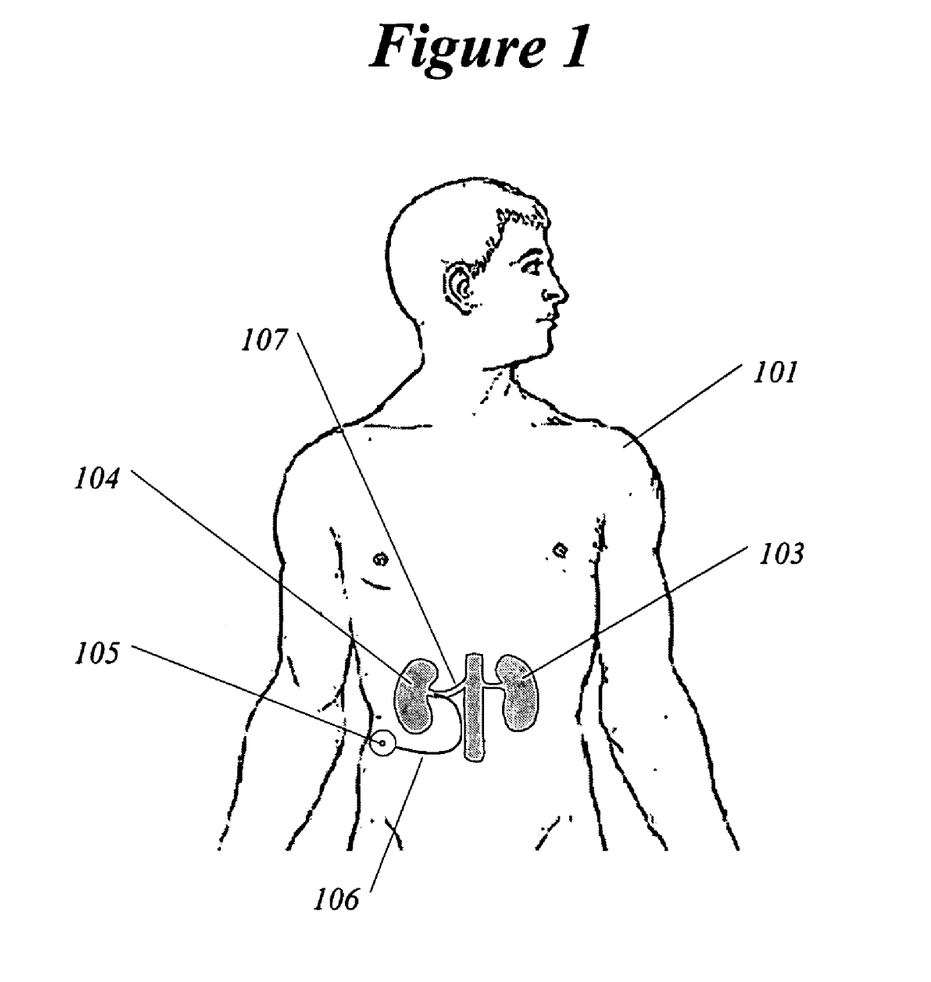
FIG. 1 illustrates the patient treated with an implanted pump embodiment of the invention.

FIG. 1 illustrates a patient 101 treated with the preferred embodiment of the invention. Patient has kidneys 103 and 104 that are bean shaped organs 12 cm long, 6 cm wide, 3 cm thick located outside and behind the peritoneal cavity. Patient is equipped with an implantable drug pump 105 implanted in the patient's side under the skin. The pump is equipped with a drug delivery catheter 106 that terminates in the area of the renal artery 107 where the delivered drug is capable of blocking the renal nerve.

Figure 2:
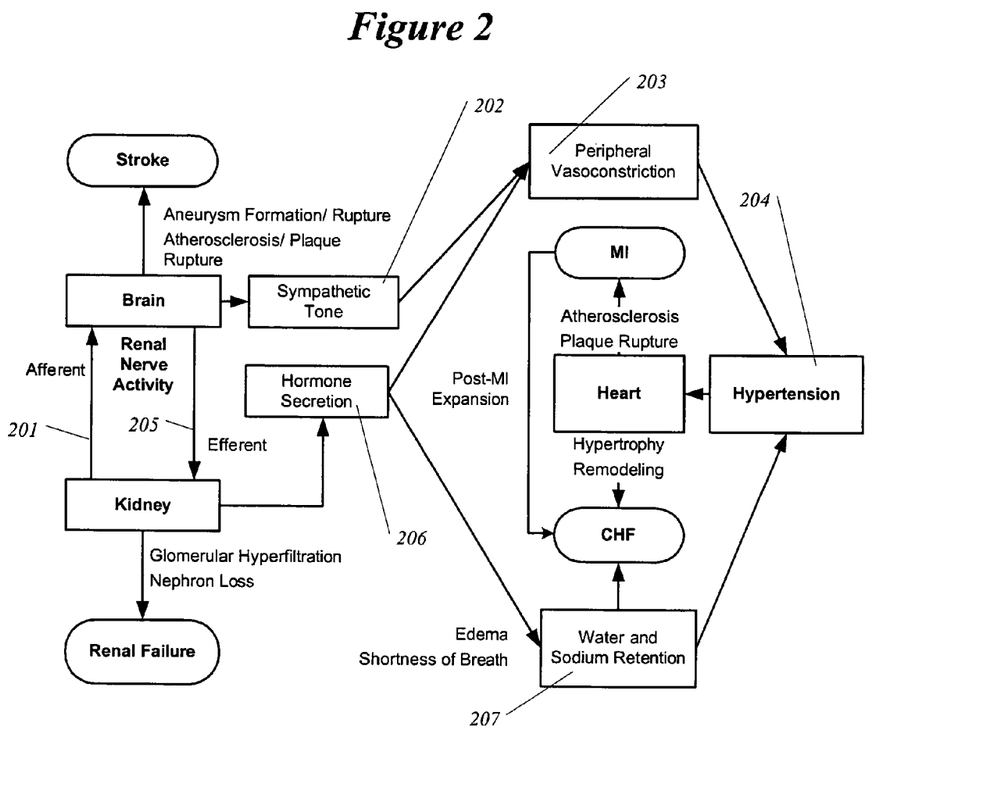
FIG. 2 illustrates the physiologic mechanisms of renal nerve modulation.

FIG. 2 illustrates the role of renal nerve activity in the progression of chronic cardiac and renal diseases. Increased renal afferent (from the kidney to the brain) nerve activity 201 results in the increased systemic sympathetic tone 202 and vasoconstriction (narrowing) 203 of blood vessels. Increased resistance of blood vessels results in hypertension 204. Hypertension is a major contributor to the progression of chronic heart failure and renal failure as well as the acute events such as strokes and myocardial infarcts. Increased renal efferent (from the brain to the kidney) nerve activity 205 results in further increased afferent renal nerve activity, secretion of the renal hormone renin 206, and reduction of renal blood flow and the decreased water and sodium excretion by the kidney. Renin contributes to systemic vasoconstriction of blood vessels 203. In combination these renal factors result in fluid retention 207 and increased workload of the heart thus contributing to the further deterioration of the patient. It should be clear from the FIG. 2 that moderation of renal nerve activity will benefit patients with heart, kidney and circulatory system (cardiorenal) diseases.

Figure 3:
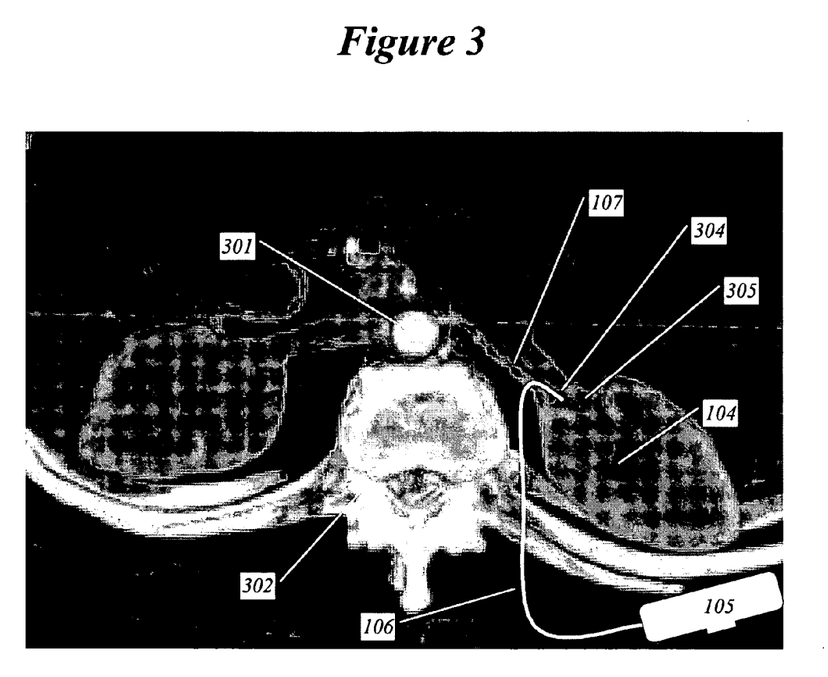
FIG. 3 illustrates anatomic positioning of the renal nerve blocking device.

FIG. 3 illustrates a preferred embodiment of the invention using a CT scan (digital X-ray) image of a human body. The pump 105 is implanted under the skin in the patient's back. The pump is equipped with the catheter 106. Tip 304 of the catheter resides near the renal artery 107. In this example, the tip 304 is shown in the hilum 305 area of the kidney where the renal blood vessels (arteries and veins) enter and exit the kidney. In clinical practice, the tip could reside in other locations within the renal periarterial space as long as the position allows the spread of the nerve blocking agent to at least a sufficient area of the nerve to achieve the required level of nerve blockade. Each kidney has an outer convex surface and an indentation on the inner side called the hilum. The hilum functions as a route of entry and exit for the blood vessels, lymph vessels, nerves and ureters of the kidney. Renal nerves follow the renal artery 107 that connects the kidney 104 to the aorta 301 shown in front of the spine 302. Kidney and renal vessels are enclosed in fat and fascia made of connective tissues that do not show well on this type of CT scan image.

It is significant that the catheter 106 can be introduced into the periarterial space under the CT guidance without surgery. The spatial resolution of modern imaging modalities such as CT, CT Fluoroscopy, Ultrasound and MRI allows an interventional radiologist to position the catheter within a millimeter from the renal artery of a human. The procedure is performed using a needle, an exchange guidewire and similar techniques commonly used in interventional radiology. The distal end of the catheter can be left outside of the body for the test period or the entire treatment if the treatment requires only a short duration. Later, if the renal nerve blocking therapy is clinically successful, an implanted pump or a simple subcutaneous port such as a commercially available Port-A-Cath device can be connected to the already implanted catheter for repeat infusions of the nerve-blocking drug.

Figure 4:
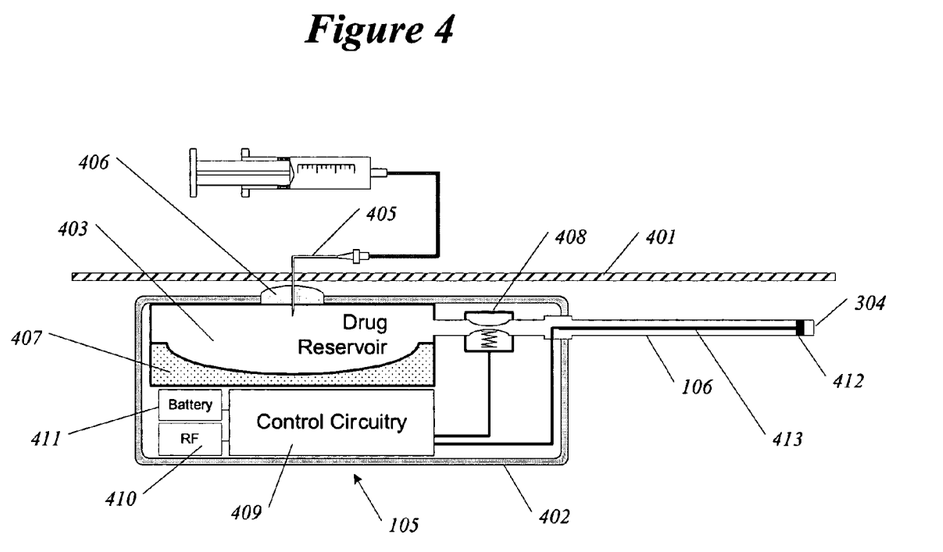
FIG. 4 illustrates an implantable drug infusion pump with a catheter electrode.

FIG. 4 illustrates a simplified design of an implantable programmable drug infusion pump. The pump 105 in implanted in a pocket under the patient's skin 401. All the mechanisms of the pump are enclosed in a titanium or polymer case 402. Drug is stored in the reservoir 403. To refill the pump a needle 405 is used to puncture the skin and the pump reservoir septum 406. Septum 406 is made of a material such as silicon that seals after the puncture. Drug is displaced from the reservoir by the compressed propellant 407. The propellant can be a chlorofluorocarbon, butane or other similar compound. The propellant acts on the drug through the elastic diaphragm 408. Alternatively, the diaphragm can act as a spring or it can be acted upon by the spring to displace the drug. The catheter 106 is in fluid communication with the reservoir 403. The propellant urges the drug from the reservoir into the catheter and through the catheter to the site of delivery, in this case, periarterial space of the renal artery and the renal nerve. To control the release of the drug, a valve 408 is placed between the reservoir and the catheter. The valve is normally closed. When it is forced open by the pump electronic control circuitry 409 for a short duration of time, a bolus of drug is released from the pump to the renal nerve-blocking site. The internal battery 411 supplies energy to the electronics and the valve. The communication electronics 410 allows the physician to reprogram the pump altering the amount and frequency of drug delivery as well as to interrogate the device. The communication electronics can be a radio-frequency RF link. All the elements described above are known to the developers of implantable drug pumps.

Programmable implantable infusion devices (also called implantable pumps) that actively meter the drug into an associated drug delivery catheter are described in the U.S. Pat. Nos. 4,692,147; 5,713,847; 5,711,326; 5,458,631; 4,360,019; 4,487,603; and 4,715,852. Alternatively, implantable infusion devices can control drug delivery by means of a rate-limiting element positioned between the drug reservoir and the delivery catheter as described in the U.S. Pat. No. 5,836,935, or by only releasing drug from the reservoir upon application of pressure to a subcutaneously positioned control device as described in U.S. Pat. Nos. 4,816,016 and 4,405,305. Implantable infusion devices have been used for intravenous, intraarterial, intrathecal, intraperitoneal, intraspinal and epidural drug delivery but not for periarterial drug infusion.

Known infusion pumps described above can be used to block the renal nerve for the purpose of treating cardiac diseases but they lack certain features needed in practical application. It is important for the physician to be able to determine that the nerve is in fact effectively blocked. In pain control applications of local anesthetics, the disappearance of the pain by itself is an indicator of an effective block. There is no natural indication of the renal nerve activity that can be simply measured. To address that problem, the pump 105 is equipped with a test electrode 412 on the tip 304 of the catheter 106. The electrode can be a single ring or multiple electrodes made of a conductive metal such as gold, stainless steel or titanium. The electrode 412 is connected to the control circuitry of the pump 409 by a conductive wire 413 integrated inside the catheter body 106. Except for the tip electrode 412 the wire is electrically insulated from the patient.

To test the effectiveness of the renal nerve block the control circuitry initiates an electric pulse to the electrode. To close the electric circuit the metal case 402 of the pump can be used as a second return electrode. Alternatively the catheter 106 can be equipped with more than one electrode. Low electric current pulse that can be in the range of 5–10 milliamps is passed through the tissue surrounding the electrode 412. If the nerve block is effective, patient will have no sensation of tingling or minor electric shock. If the block is ineffective, the nerves in the surrounding tissue will conduct the pulse, causing pain that the patient then reports to the physician and the physician will be able to make adjustments to therapy such as, for example, increase the dose of drug delivered by the pump.

This aspect is similar to the surgical technique used by anesthesiologists to establish short term invasive nerve blocks during surgery. Before the start of the surgery, the anesthesiologist places a needle precisely on the nerve or plexus. To do this, a specially designed electrical nerve stimulator is used. The nerve stimulator delivers a very small electrical current, too small to be felt, to the nerve, which causes twitching of the particular muscles supplied by that nerve or plexus of nerves. In this example, the nerve serves as nothing more than a sophisticated "electrical wire", which is now conducting the current delivered by an electrical device to the muscles, in place of the normally conducted current originating from the brain. The patient will therefore experience small muscle twitches in the muscles supplied by that nerve similar to when your eye is twitching. This technique has never been previously applied to an implanted device. In the proposed invention, the physician will be able to perform the nerve block test in their office, without sophisticated surgical techniques and sterile environment. The external programmer device will initiate a command sequence that will be received by the electronics of the implanted pump using RF waves.

In an alternate embodiment, the catheter can have two or more sets of electrodes, at least one set proximal to and at least one set distal to the area of renal nerve blockade. Each set of electrodes is in sufficient proximity to the renal nerve so that it can either sense intrinsic nerve activity or stimulate nerve activity. It is clear that if the pump control circuitry initiates and electrical pulse to a one set of electrodes on one side of the block and does not record a corresponding and appropriately timed signal on the opposite side of the block, then the drug is effective in creating the nerve block. Conversely, if the electrical activity is sensed, more drug must be infused to create the desired block. It is also clear that this information can be used as feedback by the control circuitry to automatically adjust the timing and/or amount of drug released.

Figure 5:
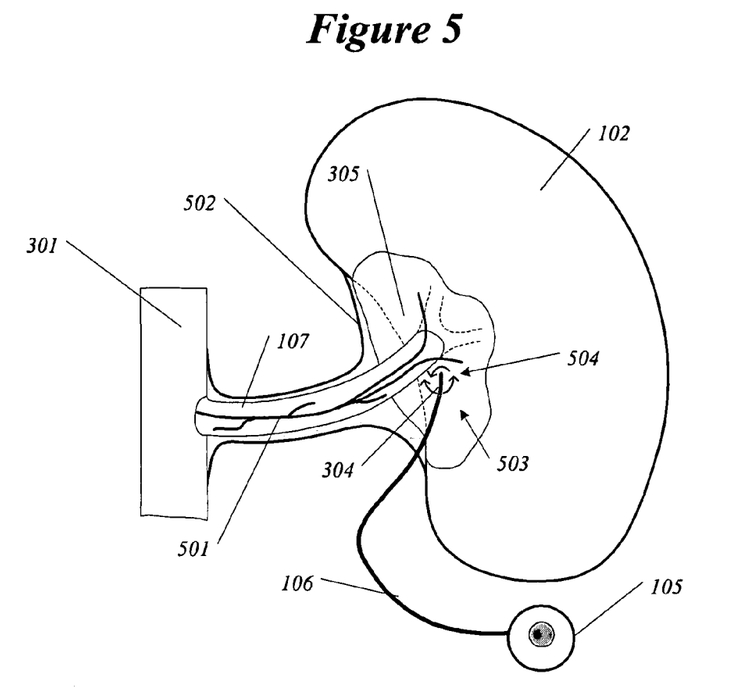
FIG. 5 illustrates the infusion of an anesthetic drug into the renal fatpad.

FIG. 5 illustrates the anatomic placement of the drug infusion catheter 106 in the periarterial space of the renal artery. Catheter 106 is shown schematically in connection to the implanted pump 105. The kidney 102 is supplied with blood by the renal artery 107 from the aorta 301. The periarterial space is defined as space immediately surrounding the renal arteries and veins along its length between the connection to the aorta and the hilum 305 of the kidney. The renal artery can branch into two or more arteries. The renal vein and its branches connecting the kidney to the vena cava of the patient share the space. These additional elements of the renal vascular system are omitted on FIG. 5 and the following figures for clarity but are presumed there.

Renal nerve 501 is shown schematically as a branching network attached to the external surface of the renal artery 107. Anatomically, the renal nerve forms one or more plexi on the external surface of the renal artery. Fibers contributing to these plexi arise from the celiac ganglion, the lowest splanchnic nerve, the aorticorenal ganglion and aortic plexus. The plexi are distributed with branches of the renal artery to vessels of the kidney, the glomeruli and tubules. The nerves from these sources, fifteen or twenty in number, have a few ganglia developed upon them. They accompany the branches of the renal artery into the kidney; some filaments are distributed to the spermatic plexus and, on the right side, to the inferior vena cava.

A fibrous connective tissue layer, called the renal capsule, encloses each kidney. Around the renal capsule is a dense deposit of adipose tissue, the renal fat pad, which protects the kidney from mechanical shock. The kidneys and the surrounding adipose tissue are anchored to the abdominal wall by a thin layer of connective tissue, the renal fascia. The periarterial space of the renal artery is externally limited by renal fascia 502 that extends between the kidney and the aorta and contains renal vessels and nerves. Renal fascia presents a natural barrier to the dissipation of the infused drug 504 that is emitted from the tip of the catheter 106. Fat fills the space between the fascia and the renal artery. In particular, there is a fat tissue layer 503 in the hilum of the kidney that surrounds the renal pedicle where arteries, nerves and veins enter the kidney. The catheter tip 304 is shown penetrating the renal fascia and the renal fat and the anesthetic drug is infused into the fatpad tissue. Although shown in the hilum of the kidney, the tip can be placed anywhere in the renal periarterial space as long as the position allows the spread of the nerve blocking agent to at least a sufficient area of nerve to achieve the required level of nerve blockade. In practice, there is an advantage to placing the tip at a location in continuity with the periarterial space fat. Anesthetic drugs such as amino ester and amino amide local anesthetics such as bupivacaine have high lipid solubility. The invention takes advantage of this. A single bolus of bupivacaine, after being infused into these areas, will be adsorbed by fat and retained at the location of the renal nerve. In this manner, the renal fat serves as storage of drug that will then be slowly released from the renal fat, and in this way, obtains the desired prolonged nerve blocking action.

Figure 6:
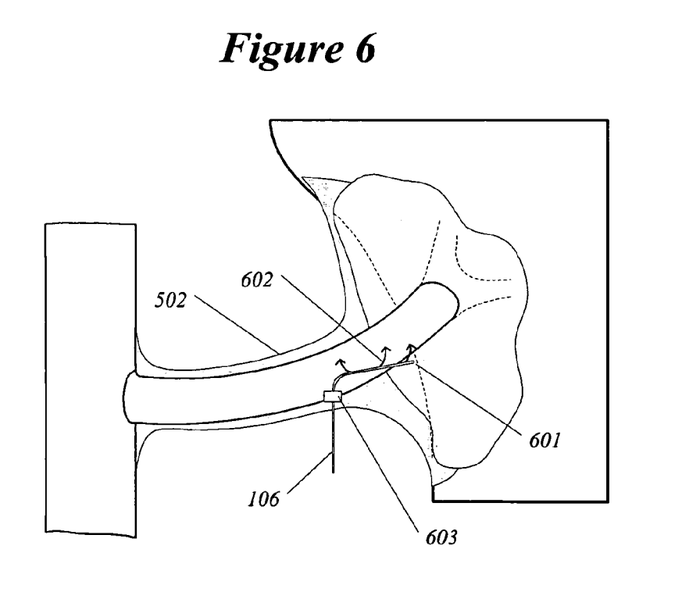
FIG. 6 illustrates a catheter with a cuff for distributed drug infusion into the periarterial space.

FIG. 6 illustrates an alternative embodiment of the invention where the catheter 106 has a sealed tip 601 but is equipped with multiple side holes or pores 602 in the wall of the catheter. The pores can be as small as a micron in diameter. Pores less than 20 microns in diameter will allow penetration of the nerve-blocking drug through the wall of the catheter and into the periarterial space, renal fat pad and ultimately to the renal nerve target. At the same time, these small pores will discourage ingrowth of tissue into the side holes and increase the probability of the catheter patency after being implanted in the body for a long time. This design helps redistribute the anesthetic in the periarterial space between the wall of the renal artery and the renal fascia 502. The catheter is equipped with a cuff 603 to encourage ingrowth of connective tissue and prevents escape of the infused drug through the puncture in the renal fascia. The cuff can be made of a natural or synthetic fiber material with pores larger than 20 microns and preferably 100 microns. For example, Dacron cuffs are commonly used in surgically implanted catheters for long term vascular access and dialysis in humans, Dacron cuffs support ingrowth of tissue, prevent dislodgment and provide a barrier to infection.

Figure 7:
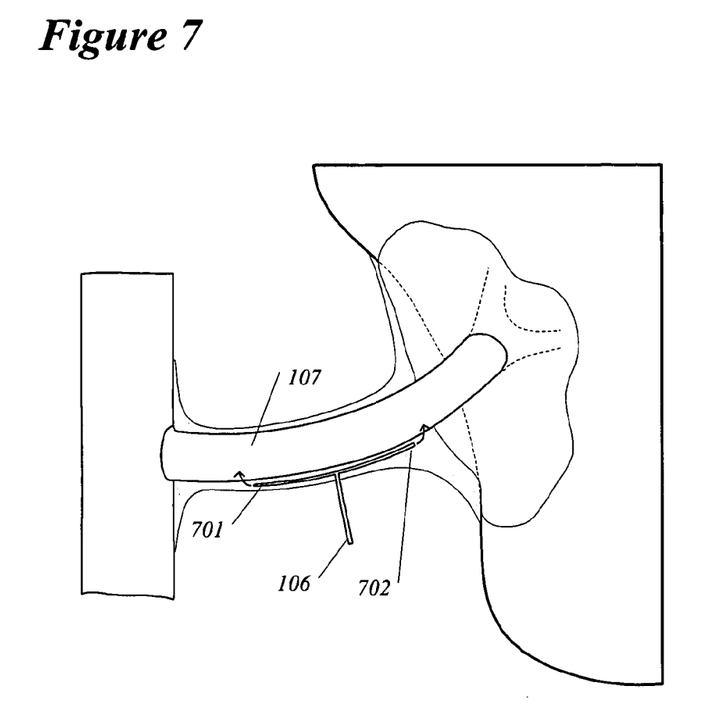
FIG. 7 illustrates a bifurcated catheter for drug infusion into the periarterial space.

FIG. 7 illustrates an embodiment of the catheter 106 that bifurcates in the periarterial space of the kidney after it enters inside the renal fascia. The internal lumen of the catheter is split between two or more branches 701 and 702. Catheter brunches can have end holes; side holes or wall pores for the delivery of medication to the renal nerve.

Figure 8:
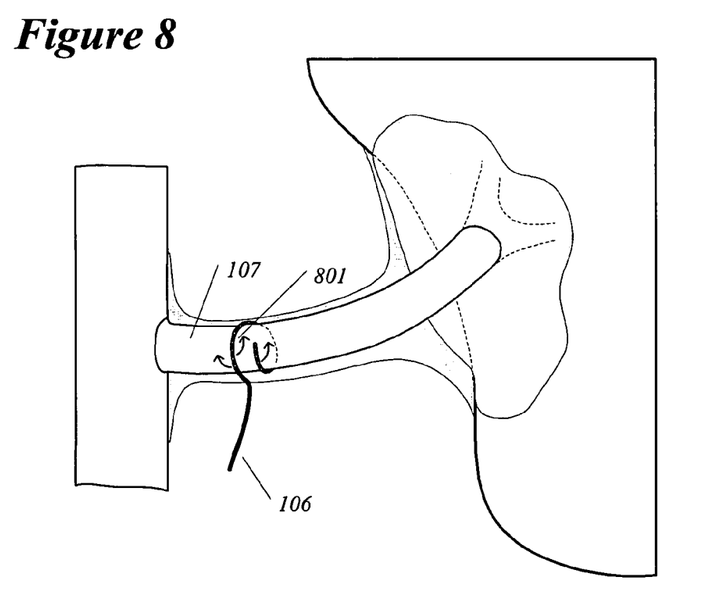
FIG. 8 illustrates a coiled catheter for drug infusion into the periarterial space.

FIG. 8 illustrates an embodiment of the catheter 106 that forms a coil 801 inside the periarterial space. The coil can be equipped with side holes or pores to evenly distribute the infused drug in the periarterial space around the renal artery.

Figure 9:
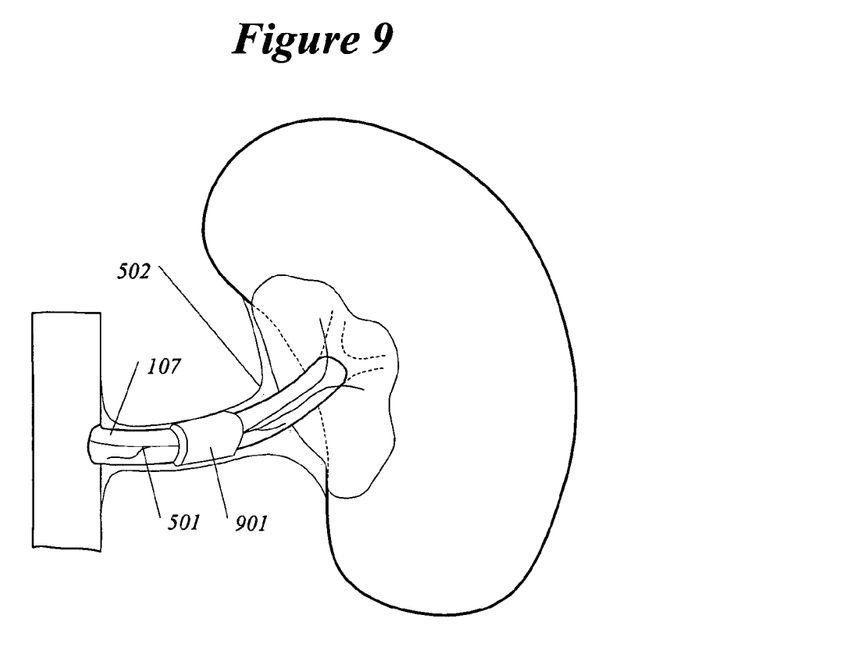
FIG. 9 illustrates a drug eluting implant in the periarterial space.

FIG. 9 illustrates an alternative preferred embodiment of the invention. The nerve blocking agent is stored in the drug eluting implant 901. The implant 901 is contained in the periarterial space after the implantation surgery. Implant can be permanent or slowly biodegradable. Prior to implantation the implant is impregnated or "loaded" with a nerve-blocking agent that is gradually released over time into the periarterial space in the amount sufficient to block the renal nerve. An implantable drug eluting implant or pellet(s) made of a nonbiodegradable polymer has the drawback of requiring both surgical implantation and removal. Use of a biocompatible, biodegradable implant overcomes deficiencies of nonbiodegradable implants. A biodegradable implant can release a drug over a long period of time with simultaneous or subsequent degradation of the polymer within the tissue into constituents, thereby avoiding any need to remove the implant. A degradable polymer can be a surface eroding polymer. A surface eroding polymer degrades only from its exterior surface, and drug release is therefore proportional to the polymer erosion rate. A suitable such polymer can be a polyanhydride. It is advantageous to have a surface eroding implant where the eroding surface faces the renal artery and the renal nerve. Other surfaces of the implant may be designed to erode at a slower rate or not erode at all that directing the drug towards the renal nerve target.

Implants for long-term drug delivery are known. For example, such implants have been used or proposed for delivering a birth control drug systemically (into circulation) or a chemotherapeutic agent to a localized breast tumor. Examples of such implantable drug delivery devices include implantable diffusion systems (see, e.g., implants such as Norplant for birth control and Zoladex for the treatment of prostate cancer) and other such systems, described of example in U.S. Pat. Nos. 5,756,115; 5,429,634; 5,843,069. Norplant is an example of a class of the drug eluding implants also called controlled release systems comprising a polymer for prolonged delivery of a therapeutic drug. Norplant is a subdermal reservoir implant comprised of a polymer can be used to release a contraceptive steroid, such as progestin, in amounts of 25–30 mg/day for up to sixty months. Norplant uses the DURIN biodegradable implant technology that is a platform for controlled delivery of drugs for periods of weeks to six months or more. DURIN can be adopted for delivery of an anesthetic into the periarterial space. The technology is based on the use of biodegradable polyester excipients, which have a proven record of safety and effectiveness in approved drug delivery and medical device products. DURIN technology is available from the DURECT Corporation of Cupertino, Calif.

Drug eluting implants generally operate by simple diffusion, e.g., the active agent diffuses through a polymeric material at a rate that is controlled by the characteristics of the active agent formulation and the polymeric material. An alternative approach involves the use of biodegradable implants, which facilitate drug delivery through degradation or erosion of the implant material that contains the drug (see, e.g., U.S. Pat. No. 5,626,862). Alternatively, the implant may be based upon an osmotically-driven device to accomplish controlled drug delivery (see, e.g., U.S. Pat. Nos. 3,987,790; 4,865,845; 5,057,318; 5,059,423; 5,112,614; 5,137,727; 5,234,692; 5,234,693; and 5,728,396). These osmotic pumps generally operate by imbibing fluid from the outside environment and releasing corresponding amounts of the therapeutic agent. Osmotic pumps suitable for the renal nerve blocking application are available from ALZA Corporation of Mountain View, Calif. under the brand name of Alzet Osmotic Pumps and the Duros implant. Duros implant is a miniature cylinder made from a titanium alloy, which protects and stabilizes the drug inside. Water enters into one end of the cylinder through a semipermeable membrane; the drug is delivered from a port at the other end of the cylinder at a controlled rate appropriate to the specific therapeutic agent. The advantage of drug eluting implants is that they can store a common anesthetic agent in concentration much higher than that used for common local anesthetic injections. Accurate delivery of small amounts of the drug via diffusion enables storage of the many months supply of the nerve-blocking agent in the implant and eliminates the need for frequent refills typical of an implanted drug pump. It is also clear that more than one drug can be released from the implant, that function in either in a complementary or inhibiting manner, to enhance or block the activity of each other.

Figure 9A:
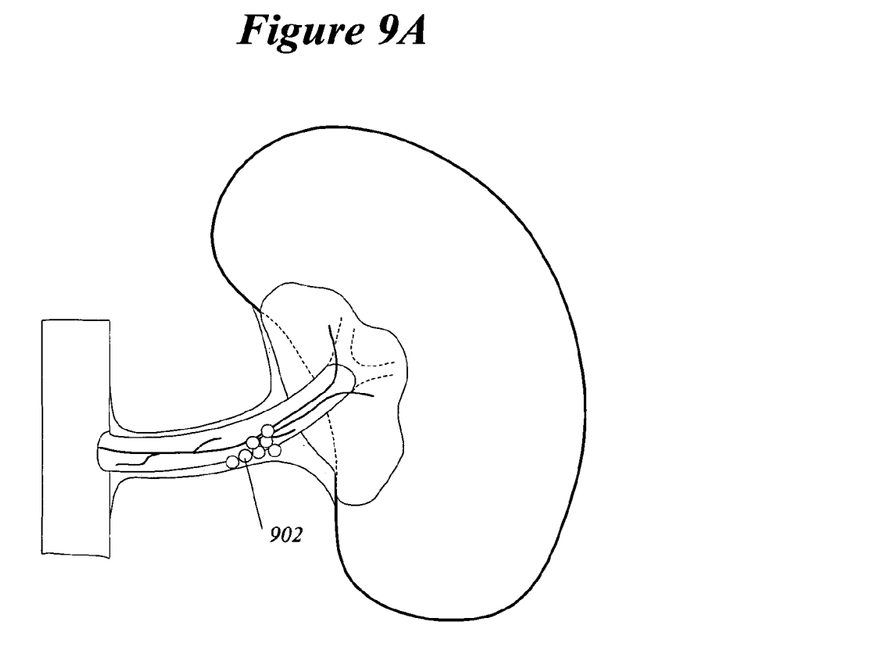
FIG. 9A illustrates a drug eluting biodegradable material in the periarterial space.

FIG. 9A illustrates an alternative embodiment of the local drug eluting system illustrated by FIG. 9. In this embodiment the sustained release of the nerve-blocking agent is accomplished by infusing or implanting a self-forming biodegradable compound impregnated with the nerve-blocking agent in the periarterial space around the renal artery. The nerve-blocking agent is delivered in a biodegradable matrix such as an injectable get or microspheres. The action of the nerve-blocking drug is thus prolonged and can be enhanced by adding other medicaments, such as steroids, that suppress inflammation at the application site. This embodiment has an advantage of allowing better distribution and conformance of the drug eluting implant to the anatomic space surrounding the renal nerve. The carrier matrix loaded with the nerve blocking drug can be applied as a patch by the surgeon to the surface of the renal artery. Then the periarterial space will be closed and the fascia repaired. Alternatively the carrier matrix can be delivered through a needle attached to an infusion device. Such needle can be inserted into the periarterial space under CT guidance as illustrated by FIG. 3. For delivery through a needle the matrix will need to be in the form of gel or injectable microspheres.

Patches and gels containing local anesthetics have been previously used for topical application to numb skin at the site of irritation or burn as well as for example during cataract eye surgery. One applicable gel is described in the U.S. Pat. No. 5,589,192 to Okabe, et al. "Gel pharmaceutical formulation for local anesthesia."

Injectable microparticles or microspheres or microcapsules loaded with drugs are also known. Injectable microspheres are made of degradable materials, such as lactic acid-glycolic acid copolymers, polycaprolactones and cholesterol among others. For example, U.S. Pat. No. 5,061,492 related to prolonged release microcapsules of a water-soluble drug in a biodegradable polymer matrix which is composed of a copolymer of glycolic acid and a lactic acid. The injectable preparation is made by preparing a water-in-oil emulsion of aqueous layer of drug and drug retaining substance and an oil layer of the polymer, thickening and then water-drying. In addition, controlled release microparticles containing glucocorticoid (steroid) agents are described, for example, by Tice et al. in U.S. Pat. No. 4,530,840. In another embodiment, the implanted microspheres are stable and do not degrade on their own. In this case, the microspheres are broken via external, directed application of an energy source, such as ultrasound, temperature or radiation. Breaking of the microspheres release the encapsulated drug and provide the desired physiologic effect, in this case, nerve blockade.

U.S. Pat. No. 5,700,485 to Berde, et al. titled "Prolonged nerve blockade by the combination of local anesthetic and glucocorticoid" describes in sufficient detail methods of manufacturing and application of biodegradable controlled release microspheres for the prolonged administration of a local anesthetic agent. The microspheres are formed of biodegradable polymers polyanhydrides, polylactic acid-glycolic acid copolymers. Local anesthetics are incorporated into the polymer. Prolonged release is obtained by incorporation of a glucocorticoid into the polymeric matrix or by co-administration of the glucocorticoid with the microspheres. Significantly U.S. Pat. No. 6,238,702 to the same authors entitled "High load formulations and methods for providing prolonged local anesthesia" described the polymer matrix that contained significantly higher concentration of local anesthetic than is normally used for injections. Since the periarterial space can anatomically accommodate an implant of substantial size nerve blocking for at least 30 days and more preferably several years is possible. U.S. Pat. No. 5,618,563 to Berde, et al. titled "Biodegradable polymer matrices for sustained delivery of local anesthetic agents" further elaborates on the biodegradable controlled release system consisting of a polymeric matrix incorporating a local anesthetic for the prolonged administration of the local anesthetic agent, and a method for the manufacture thereof.

Figure 10:
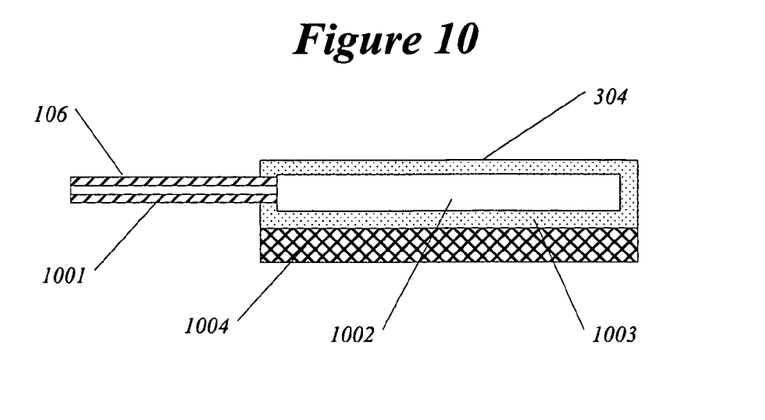
FIG. 10 illustrates a porous drug infusion catheter.

FIG. 10 illustrates the design of the drug delivery catheter for the invention that improves fixation of the catheter and distribution of the infused drug in the periarterial space. After the implantation an implant and the surrounding tissue undergo changes. It is the purpose of this part of the invention to improve the interface of the drug delivery device to maximize the effect of the drug on the nerve while minimizing the amount.

The human body acts spontaneously to reject or encapsulate any foreign object, which has been introduced into the body or a specific bodily organ. In some cases, encapsulation will impede or halt drug infusion. In others, the delivery fluid will reflux from the tissue through a space opened between the exterior of the catheter and the tissue of the bore in which the catheter is received. Either of these results will greatly diminish the effect of direct infusion of medicaments on affected body tissue. Thus, the body's own natural defense systems thus tend to frustrate the procedure. The reaction of living tissue to an implant can take a number of different forms. For example, the initial response to the surgical trauma of implantation is usually called the acute inflammatory reaction and is characterized by an invasion of polymorphonuclear leukocytes (PMNs). The acute inflammatory reaction is followed by the chronic inflammatory reaction, which is characterized by the presence of numerous macrophages and lymphocytes, some monocytes and granulocytes. Fibroblasts also begin accumulating in the vicinity of the implant and begin producing a matrix of collagen. The fibroblasts and collagen form a connective tissue capsule around the implant and the chronic inflammatory cells to effectively isolate the implant and these cells from the rest of the body. Connective tissue consisting of a fine network of collagen with active producing fibroblasts accompanied by chronic inflammatory cells, capillaries and blood vessels is referred to collectively as granulation tissue.

Thus, when a material is implanted into a soft tissue bed of a living organism such as a human or an animal, a granulation tissue capsule is formed around the implant material consisting of inflammatory cells, immature fibroblasts and blood vessels. This tissue capsule usually increases in thickness with time and contracts around the implant, deforming the implantation site, and possibly the implant itself depending upon the rigidity of the implant.

Implant illustrated by FIG. 10 is the tip 304 of the drug delivery catheter 106 connected to the implanted drug pump explained earlier in this application. The tip 304 is in the fluid communication with the internal lumen 1001 of the catheter and is shown with an internal cavity 1002 to which the nerve-blocking drug is delivered by the pump 104 (See FIG. 4). The tip is made out of the porous material, preferably a porous plastic such as for example PTFE. It is known that, when the implant is porous with pore entry diameters larger than approximately 20 microns, tissue grows into these pores. This phenomenon appears desirable to many medical device application because it makes an implant one with the implanted organ and in theory it allows tissue ingrowth into the implant and reduces capsular contraction. For example, U.S. Pat. No. 4,011,861 to Enger discloses an implantable electric terminal which has pores preferably in the range of about 10 to 500 microns so that blood vessels and tissue can grow into the pores.

The embodiment illustrated by FIG. 10 combines a material with small pores, preferably less than 20 microns 304 designed to discourage the tissue ingrowth and a material with larger pores, preferably larger than 20 microns 1004 to encourage tissue ingrowth. Material 1003 allows free diffusion and convection of the drug from the cavity 1002 to the periarterial space. Material 1004 encourages the natural fixation of the catheter tip 304 so that it will not be dislodged by motion and migrate out of the periarterial space.

Figure 11:
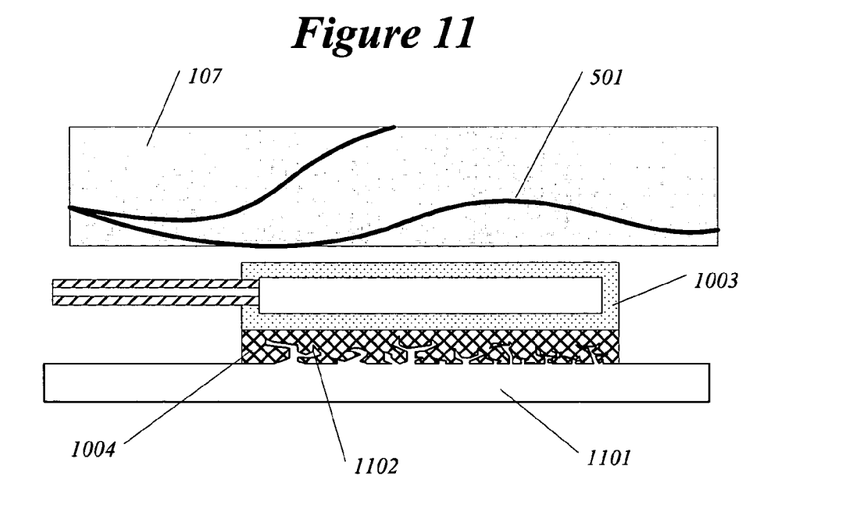
FIG. 11 illustrates a drug infusion catheter with tissue ingrowth.

FIG. 11 illustrates the catheter tip made of porous materials. It shows the surrounding tissue 1101 ingrowth 1102 into the large pore implant 1004 section. The small pore section 1003 is oriented to direct the drug infusion towards the renal artery 107 and the renal nerve 501.

Figure 12:
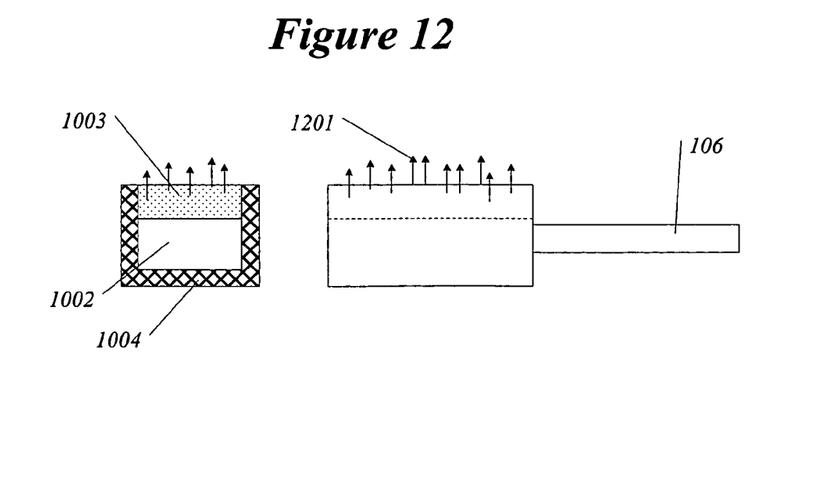
FIG. 12 illustrates the drug infusion catheter that directs the drug towards the renal nerve.

FIG. 12 further illustrates an embodiment of the porous tip of the catheter 106 for directional drug delivery. The portion of the implant that surrounds the drug filled cavity 1002 and that is oriented away from the renal nerve is made of the material 1004 that is impermeable to drug. Portion of the implant that is oriented towards the renal nerve (on the surface of the renal artery) 1003 is made of the material that is permeable to the nerve blocking agent. Drug flux 1201 is shown as unidirectional therefore directing the therapy towards the site and minimizing the loss of the drug.

Figure 13:
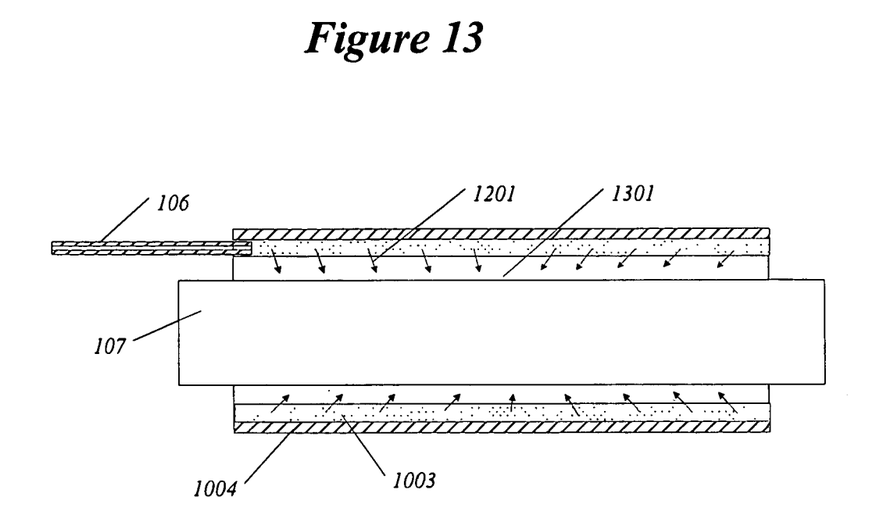
FIG. 13 illustrates the drug infusion catheter that overlaps the renal artery and directs the drug infusion towards the renal nerve.
Figure 14:
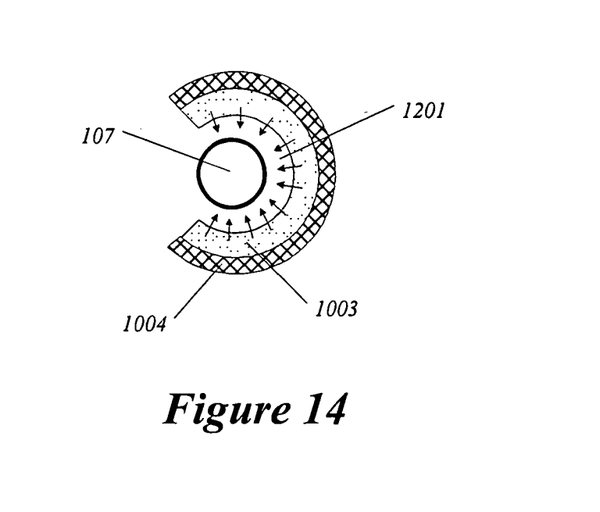
FIG. 14 is a cross-sectional view of the catheter and artery shown in FIG. 13.

FIGS. 13 and 14 further illustrate an embodiment of the porous tip of the catheter 106 that at least partially encloses or envelopes the renal artery 107 with the intention of further directing the drug delivery towards the renal nerve. The tip forms a multi-layer cuff around the artery. The outer shell 1004 of the cuff is made of the material that is impermeable to the infused drug to prevent dissipation of the said drug away from the renal nerve. The material 1004 can also have large pores to encourage ingrowth and fixation of the implant. The inner layer 1003 is made of material permeable to the nerve-blocking drug. It is in fluid communication with the delivery catheter 106. The layer 1003 can be equipped with internal channels to facilitate equal distribution of drug 1201 in the space 1301 between the cuff and the artery 107.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for at least partially blocking a renal nerve of a kidney of a human patient for the purpose of treating a cardiorenal disease comprising:
   a. implanting a drug delivery catheter in a periarterial space of the kidney;
   b. implanting a drug infusion pump in the body of the patient;
   c. connecting the drug infusion pump to the said catheter; and
   d. delivering a nerve-blocking agent to the periarterial space.

2. A method as in claim 1 including an additional step of applying an electric charge to the implanted catheter to determine the effectiveness of the blocking of the renal nerve.

3. A method as in claim 2 where the electric charge is applied by the drug infusion pump.

4. A method as in claim 1 where the nerve-blocking agent is selected from the group consisting of a local anesthetic, ketamine, tricyclic antidepressant and neurotoxin.

5. A method as in claim 1 where the nerve-blocking agent is combined with a steroid.

6. A method for at least partially blocking a renal nerve of a kidney of a human patient for the purpose of treating a cardiorenal disease comprising:
   a. implanting a drug delivery device in a periarterial space of the kidney; and
   b. delivering a nerve-blocking drug to the periarterial space.

7. The method of claim 6 wherein the drug delivery device comprises a drug delivery catheter.

8. A method as in claim 7 wherein the catheter is implanted in the renal fatpad.

9. A method as in claim 7 where the catheter implanted in the periarterial space is made of a porous material permeable to the nerve-blocking agent.

10. A method as in claim 7 where the catheter is coiled around the renal artery.

11. A method as in claim 7 where the catheter is made of a porous material adapted to receive ingrowth of tissue.

12. A method as in claim 6 where the step of delivering a nerve-blocking drug to the periarterial space is performed periodically.

13. The method of claim 6 wherein the drug delivery device comprises a drug eluting device.

14. A method as in claim 13 where the implantable drug eluting device is a biodegradable polymeric matrix.

15. A method as in claim 13 where the implantable drug eluting device comprises a biodegradable gel.

16. A method as in claim 13 where the implantable drug eluting device comprises microspheres.

17. A method as in claim 13 where the implantable drug eluting device is shaped to surround the renal artery.

18. A method as in claim 13 where the implantable drug eluting device comprises osmotic pump.

19. A method as in claim 13 where the implantable drug eluting device comprises self forming biodegradable compound.

20. A method as in claim 6 where the nerve-blocking drug is combined with a steroid.

21. A method as in claim 13 where the implantable drug eluting device comprises a patch on the renal artery.

22. A method as in claim 6 where the nerve-blocking drug is selected from the group consisting of a local anesthetic, ketamine, tricyclic antidepressant and neurotoxin.

23. A method for reducing myocardial infarct expansion by at least partially blocking a renal nerve of a kidney of a human patient comprising the steps of:
   a. implanting a drug eluting device in a periarterial space of the kidney; and
   b. delivering a nerve-blocking drug to the periarterial space.

24. A method for reducing myocardial infarct expansion by at least partially blocking a renal nerve of a kidney of a human patient comprising:
   a. implanting a drug delivery catheter in a periarterial space of the kidney;
   b. implanting a drug infusion port in the body of the patient;
   c. connecting the drug infusion pump to the said port; and
   d. delivering a nerve-blocking agent to the periarterial space.

25. A method for reducing myocardial infarct expansion by at least partially blocking a renal nerve of a kidney of a human patient comprising:
   a. injecting a nerve blocking drug into a periarterial space of the kidney;
   b. blocking the renal nerve for the duration of action of the nerve blocking drug; and
   c. repeating steps a and b for the duration of the infarct expansion.

* * * * *